United States Patent
Glodde

(10) Patent No.: US 8,039,194 B2
(45) Date of Patent: Oct. 18, 2011

(54) PHOTOACID GENERATORS FOR EXTREME ULTRAVIOLET LITHOGRAPHY

(75) Inventor: Martin Glodde, Mahawah, NJ (US)

(73) Assignee: Intermatinal Business Machines Corporation, Armonk, NY (US)

( * ) Notice: Subject to any disclaimer, the term of this patent is extended or adjusted under 35 U.S.C. 154(b) by 672 days.

(21) Appl. No.: 11/970,827

(22) Filed: Jan. 8, 2008

(65) Prior Publication Data

US 2009/0176175 A1 Jul. 9, 2009

(51) Int. Cl.
*G03F 7/004* (2006.01)
*G03F 7/30* (2006.01)
*C07C 23/08* (2006.01)
*C07C 23/18* (2006.01)
*C07C 23/34* (2006.01)
*C07C 23/44* (2006.01)

(52) U.S. Cl. .............. 430/270.1; 430/326; 558/427; 558/432; 570/183; 570/187

(58) Field of Classification Search ........... 430/270.1, 430/326; 558/427, 432; 570/183, 187
See application file for complete search history.

(56) References Cited

U.S. PATENT DOCUMENTS

| 3,853,943 | A | 12/1974 | Webster | ............ 558/432 |
| 6,093,753 | A | 7/2000 | Takahashi | |
| 6,358,665 | B1 * | 3/2002 | Pawlowski et al. | ........ 430/270.1 |
| 6,387,587 | B1 * | 5/2002 | Oomori et al. | ............ 430/270.1 |
| 6,849,374 | B2 | 2/2005 | Cameron | |
| 7,202,015 | B2 | 4/2007 | Kanna et al. | |
| 7,214,465 | B2 | 5/2007 | Nakao et al. | |
| 7,214,467 | B2 | 5/2007 | Kanna et al. | |
| 7,232,640 | B1 | 6/2007 | Mizutani et al. | |
| 7,655,379 | B2 * | 2/2010 | Glodde et al. | ............ 430/270.1 |
| 2003/0194639 | A1 * | 10/2003 | Miya et al. | ............... 430/270.1 |
| 2004/0023163 | A1 * | 2/2004 | Yukawa et al. | ............... 430/326 |
| 2005/0221220 | A1 | 10/2005 | Meagley | |
| 2007/0128547 | A1 | 6/2007 | Mizutani et al. | |

OTHER PUBLICATIONS

U.S. Appl. No. 11/970,731, filed Jan. 8, 2008, Martin Giodde, et al.
EP 1338921, Mizutani, et al.
Wallraff, et al., Lithographic Imaging Techniques . . . , *Chem. Rev.*, 1999, 99, 1801-1821.
Crivello, The Discovery and Development of Onium . . . , Jour. Of Pol. Sci.: Part A: Pol. Chem., vol. 37, 4241-4254 (1999).
Vianello, et al. ,Towards highly powerful neutral organic . superacids . . . , Tetrahedron 61 (2005) 9381-9390.
Vianello, et al. , In Search of Ultrastrong Bronsted Neutral . . . , Superacids . . . , *Chem. Eur. J.* 2004, 10, 5751-5760.
*J. Org. Chem.* 1958, 53, 5571-5573.
Richardson et al., Exploration of the Pentacyano-*cycol*-pewntadiene ion . . . , *Chem. Commun.*, 2004, 706-707.
Simmons et al., Thiacyanocarbons . . . , *J. Org. Chem.* ,1980, 45, 5113-5121.

* cited by examiner

*Primary Examiner* — John S Chu
(74) *Attorney, Agent, or Firm* — Robert J. Eichelburg; The Law Offices of Robert J. Eichelburg

(57) ABSTRACT

A photoacid generator $P^+ A^-$ comprises (a) an antenna group $P^+$ comprising atoms with high EUV photoabsorption cross-sections according to FIG. 1 and $A^-$ anions; or (b) an antenna group $P^+$ and $A^-$ comprising anions with low photoabsorption cross-sections for EUV; or (c) an antenna group $P^+$, comprising atoms with high EUV photoabsorption cross-sections according to FIG. 1 and $A^-$ comprising anions with low photoabsorption cross-sections for EUV. Novel compounds comprise DTFPIO PFBuS, and DTBPIO CN5.

30 Claims, 4 Drawing Sheets

PHOTOACID GENERATORS FOR EXTREME ULTRAVIOLET LITHOGRAPHY

FIELD OF THE INVENTION

The present invention relates to polymer formulations used in extreme ultraviolet (EUV) lithography and photolithography. More specifically, this invention relates to the field of Photoacid Generators (PAGs) used in such polymer formulations.

BACKGROUND OF THE INVENTION AND RELATED ART

The dependency of the resolution of optical lithography on the wavelength and the numerical aperture has continuously been reflected by the further development of corresponding exposure tools. Due to its significantly shorter wavelength, EUV lithography at 13.5 nm (92 eV) is therefore a promising technology for the next generation lithography. It has been demonstrated that chemically amplified resists (CAR) can achieve a resolution of 25 nm half-pitch line:space features with interferometric EUV lithography (J. W. Thackeray, et al., Proc. SPIE 6517, 651719 (2007)). However, source power and resist performances are far from the set targets, thus leading to very slow photospeed. For example, the targeted source power for EUV manufacturing tools is 180 W delivered to the illuminator optics, while currently used sources struggle to reach even intensities as low as 10 W at intermediate focus. Similar to the tool, EUV resists also need significant improvements to reach the targeted performance. For example, the targeted dose for a resolution of 32 nm is 10 mJ/cm$^2$ and the line width roughness is 1.7 nm. Currently investigated resist systems are far from these values. Due to the present issues with EUV source power, resist sensitivity comprises one of the main areas where improvement is required.

In chemically amplified resists (H. Ito, *Adv. Polym, Sci.* 2005, 172, 37; G. Wallraff, W. Hinsberg, *Chem. Rev.* 1999, 99, 1801), PAGs (J. Crivello, *J. Polym. Sci. Part A: Polym. Chem.* 1999, 37, 4241; H. Ito, C. G. Wilson, Polym. Eng. Sci. 23, 1012 (1983)) play a key role in imaging. In conventional optical lithography, CAR formulations contain a nearly transparent polymer matrix, a PAG and additional compounds, such as base quenchers, in smaller quantities. PAGs are non-acidic molecules that absorb photons and subsequently form acid via a photochemical decomposition. Acid is only formed in illuminated regions of the resists and only in these regions, the resist polymer becomes soluble (usually after baking) in basic developers.

Traditional, commercially available PAGs are for example triphenylsulfonium nonafluorobutanesulfonate (1; "TPS PFBuS") or bis(4-tert-butyl-phenyl) iodonium nonafluorobutanesulfonate (2; "DTBPIO PFBuS") having the following structure:

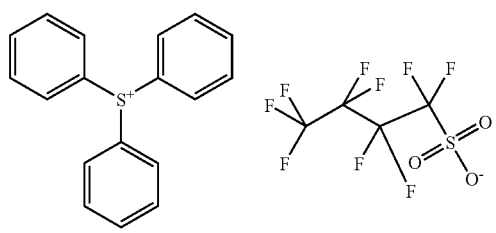

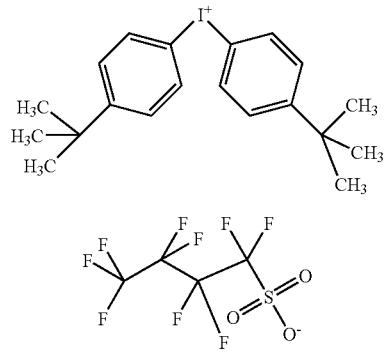

Some less commonly used, commercially available PAGs have less fluorine in the anion, such as TPS camphorsulfonate (3). However, the corresponding acid, camphorsulfonic acid, is not as strong as nonafluorobutanesulfonic acid. Moreover, the cation is still not very absorbing at 13.5 nm.

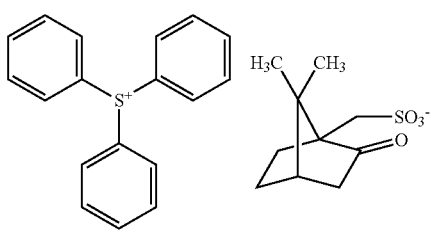

Li et al., U.S. Pat. No. 7,235,342, col. 14, line 23 to col. 15, line 2 disclose other typical PAGs used in the related art.

While the absorption of photons whose energy ranges from deep ultraviolet (~150 nm) to near infrared (~850 nm) by organic molecules, thus by PAGs, depends on the existence of certain chemical bonds, the absorption of EUV light is characterized by photoabsorption cross-sections that depend on the atomic composition of the compound which varies by atom (FIG. 1).

It is known that EUV photons are also absorbed by the resist polymers and other components and not just by the PAG. (P. Dentinger, et al., Proc. SPIE 3997, 588 (2000)). Under EUV irradiation, acid therefore may be generated by secondary processes as well and not only by direct hits of the PAG by the photons. (T. Kozawa, et al., Jpn. J. Appl. Phys. 31, 4301 (1992)) However, literature reports also indicate a strong PAG structure dependence on the acid generation efficiency in EUV light. (C. M. Szmanda, et al., J. Vac. Sci. Technol, B 17(6), 3356 (1999); T. Watanabe, et al., Jpn. J. Appl. Phys. 44, 5866 (2005))

Ionic PAGs have the general structure P$^+$ A$^-$, where P$^+$ decomposes into protons (H$^+$) upon irradiation with photons, while A$^-$ remains unchanged and forms the acid H$^+$ A$^-$. In an efficient PAG, P$^+$ therefore strongly absorbs the photons of interest, while A$^-$ does not. In contrast, if A$^-$ absorbs too many photons, the acid generation efficiency may decrease because this decreases the amount of photons that could otherwise reach P$^+$, or because A$^-$ may decompose as a consequence of photon absorption and therefore weakens the generated acid.

Commercially available PAGs, such as compounds 1, 2 and 3, commonly used in polymer formulations for optical lithography and presently used in EUV lithography, do not have an EUV-optimized atomic composition. For example, in the commonly used PAG triphenylsulfonium perfluorobutane-sulfonate (1, TPS PFBUS), where $P^+$ comprises the triphenyl-sulfonium cation and $A^-$ comprises the perfluorobutane-sulfonate anion, the EUV photoabsorption cross-section of $P^+$ is one order of magnitude lower than that of $A^-$ (FIG. 2). In the case of bis(t-butylphenyl)iodonium perfluorobutanesulfonate (2; DTBPIO PFBuS), the photoabsorption cross-section of $P^+$ is still almost one order of magnitude lower than that of $A^-$, though $P^+$ contains the highly EUV-absorbing iodine atom. To overcompensate lack of optimum EUV sensitivity, resist formulations with much higher PAG loadings than typical for photolithographic applications are used. This can lead to increased line edge roughness and high resist outgassing.

RELATED PATENTS AND U.S. PATENT APPLICATIONS

The following references include related art teachings:
O. Webster, U.S. Pat. No. 3,853,943;
R.P. Meagley, United States Patent Appl. 2005/0221220;
J.F. Cameron, U.S. Pat. No. 6,849,374;
K. Mizutani, et al., U.S. Pat. No. 7,232,640;
H. Nakao, et al., U.S. Pat. No. 7,214,465;
K. Mizutani, et al., European Patent Application EP 1338921;
S. Kanna, et al., U.S. Pat. No. 7,214,467;
S. Kanna, et al., U.S. Pat. No. 7,202,015;
K. Mizutani, et al., United States Patent Application 2007/0128547
Glodde et al., U.S. Pat. No. 7,655,379.

SUMMARY OF THE INVENTION

The foregoing indicates a need for an improved process for lithographic imaging, such as lithographic imaging using EUV irradiation (wavelength: <150 nm), particularly with respect to the photospeed obtained in such lithographic image processing, and the formulation and use of photoresists having PAGs that are systemically optimized for absorption characteristics required for most commonly used EUV photons (13.5 nm).

Accordingly, the present invention provides such a process and formulations that address these needs to not only provide advantages over the related art, but also to substantially obviate one or more of the foregoing and other limitations and disadvantages of the related art, such as limited resist sensitivity, decreased acid generation efficiency of PAGs, and resist formulations with much higher PAG loadings than typical for photolithographic applications, and the concomitant problems of bad line edge roughness (LER) and high outgassing from the decomposed PAG molecules.

The description that follows sets forth features and advantages of the invention apparent not only from the description but also by practicing the invention. The written description, drawings, abstract of the disclosure, and the claims, or as any of the foregoing may be subsequently amended will set forth additional features and advantages of the invention and point out the objectives and other advantages of the invention showing how they may be realized and obtained.

To achieve these and other advantages, and in accordance with the purpose of the invention as embodied and broadly described herein, the invention comprises novel PAGs and an improved method for lithographic imaging using these PAGs, such as lithographic imaging using EUV irradiation, including such imaging that focuses on the photospeed obtained in such lithographic imaging processes. The present invention comprises the formulation and use of photoresists employing these PAGs that are systematically optimized for absorption characteristics required for EUV photons. Incorporation of these PAGs can increase the EUV photospeed of photoresists.

In one aspect, the present invention comprises a photoresist formulation comprising:

(a) a resist polymer that is originally insoluble in aqueous, alkaline developers, but becomes soluble in these developers upon reaction with acid, under conditions specific for the particular resist polymer;

(b) an ionic photoacid generator $P^+ A^-$, in which $P^+$ contains atoms with high EUV photoabsorption cross-sections ("high" in a broader fashion means: atom-averaged EUV absorption cross-section $>5 \times 10^5$ $cm^2$/mol; in a narrower fashion: $>10^6$ $cm^2$/mol, as calculated according to FIG. 1); examples; (see below in paragraph [0016]);

(c) a small amount of a base quencher, commonly used in the art (see example below in paragraph [0016]), with "small" referring to typical PAG:base molar ratios anywhere from about 1:0.05 to about 1:0.2.

In another aspect, the invention comprises a photoacid generator compound $P^+ A^-$, comprising:

a) an antenna group $P^+$ comprising an atom with high EUV photoabsorption cross-sections according to FIG. 1 and $A^-$ comprising an anion; or b) b) an antenna group $P^+$ comprising a cation commonly used in the art and $A^-$, an anion with low EUV photoabsorption cross-sections; or c) an antenna group $P^+$ comprising an atom with high EUV photoabsorption cross-sections according to FIG. 1 and $A^-$, an anion with low EUV photoabsorption cross-sections.

In a further aspect, the invention relates to a photoacid generator compound $P^+ A^-$, comprising an antenna group $P^+$ comprising a cation with atom-averaged EUV photoabsorption cross-sections, and $A^-$ comprising an anion with atom-averaged EUV photoabsorption cross-sections; wherein the atom-averaged EUV photoabsorption cross-sections of said antenna group $P^+$ are greater than or substantially the same as the atom-averaged $A^-$ EUV photoabsorption cross-sections.

In the invention, including the aspect of the invention described immediately above, the resist polymer comprises one having an ethylenic backbone. In one embodiment, the polymer comprises vinyl, acrylate and/or methacrylate monomeric units. The backbone of the polymer comprises a backbone free of unsaturated carbon bonds. In general, the photoresist compositions of the invention are not limited to any specific imaging polymer. In one embodiment, the imaging polymer is one suitable for use in EUV lithography (<150 nm; preferred 13.5 nm).

The imaging polymer may be either positive-tone or negative-tone and in one embodiment comprises a polymer capable of undergoing chemical transformations upon exposure of the photoresist composition to UV light whereby a differential in the solubility of the polymer in either the exposed regions or the unexposed regions is created. That is, the base polymers employed in the present invention include any acid sensitive polymer having acid sensitive side groups which can undergo catalytic cleavage in the presence of an acid generated by the inventive photoacid generator. In one embodiment, the polymers comprise those where at least one of said sensitive side groups comprise polycyclic side groups.

The acid sensitive side groups of the polymers may contain a lactone moiety or may be protected with various acid labile protecting groups that are conventional and well known in the art. Such protecting groups comprise groups requiring high activation energy (e.g. tert-butyl ester or tert-butyl carbonyl groups), low activation energy (e.g. acetal, ketal, or silylethers), or a combination of both. In another embodiment, the imaging polymers comprise poly([N-(trifluoromethysulfonyl)methacrylamide]-co-[2-methyl-2-adamantyl methacrylate]-co-[5-methacryloyloxy-2,6-norbornane carbolactone]) ("S1"), poly([2-methyl-2-adamantyl methacrylate]-co-[5-methacryloyloxy-2,6-norbornane carbolactone] ("MADMA -NORLAC") and, for embodiments where 248 nm (KrF) radiation is used, poly(4-hydroxystyrene-co-tert -butyl acrylate) (65/35) ("ESCAP").

The photoacid generator has the general structure $P^+ A^-$, where $P^+$ comprises an organic cation of the general structure $R_1R_2R_3 Y^+$, or an organic halonium cation of the general structure $R_1R_2 X^+$, where $Y^+$ comprises O, S, Se, or Te, and $X^+$ comprises a halogen, such as I, and $R_1$, $R_2$ and $R_3$ comprise aliphatic or aromatic moieties that can be further substituted with common substituents, e.g., substituents comprising atoms with a high EUV photoabsorption cross-section (in the sense as described herein) such as I, Se, F, O (examples for $P^+$ include phenyl-bis(pentafluorophenyl)sulfonium ($7.76 \times 10^5$ cm$^2$/mol, atom-avg.), diphenyl-pentafluorophenylselenium ($5.48 \times 10^5$ cm$^2$/mol, atom-avg.) and bis(2,4,6-trifluorophenyl)iodonium (DTFPIO) ($1.3 \times 10^5$ cm$^2$/mol, atom-avg.)); and $A^-$ comprises the anion of a strong acid, for example $R-SO_3^-$, where R comprises an aryl or alkyl group, unsubstituted or at least partially substituted by common withdrawing atoms or moieties, such as fluorine; examples of such anions are triflate $CF_3-SO_3^-$, perfluorobutanesulfonate (PFBUS) $C_4F_9-SO_3^-$, perfluorooctanesulfonate $C_8F_{17}-SO_3^-$. The base quencher is selected from a group of compounds, comprising amines, t-butoxycarbonyl-protected amines or quaternary ammonium salts. Examples of such amines are triethylamine, pyrrolidine, trihexylamine; examples of t-butoxycarbonyl-protected amines are t-butoxycarbonyl-diethylamine, t-butoxycarbonyl-pyrrolidine, and t-butoxycarbonyl-dihexylamine; examples of quaternary ammonium salts are tetramethylammonium hydroxide, tetraethylammonium hydroxide and tetrabutylammonium hydroxide.

In another aspect, the present invention comprises a photoresist formulation comprising:

(a) a resist polymer that is originally insoluble in aqueous, alkaline developers, but becomes soluble in the developer upon reaction with acid, under conditions specific for the particular resist polymer;

(b) an ionic photoacid generator $P^+ A^-$, in which in which $P^+$ contains atoms with high EUV photoabsorption cross-sections (definition of "high" set forth herein) and $A^-$ contains atoms with low EUV photoabsorption cross-sections. ("low" means: atom-averaged EUV absorption cross-section $<5 \times 10^5$ cm$^2$/mol, as calculated according to FIG. 1; (examples set forth herein).

(c) a small amount of a base quencher, as defined in paragraph [0016]. In these formulations, we employ a small amount of a base quencher which means, e.g., an amount of a base sufficient to react with any acids that migrated into unexposed areas during post-exposure bake employed in a photolithographic process according to the invention.

In the invention, including the aspect of the invention described immediately above, the resist polymer comprises polymers as described herein. The photoacid generator has the general structure $P^+ A^-$, where $P^+$ comprises an organic cation of the general structure $R_1R_2R_{3Y} Y^+$, or an organic halonium cation of the general structure $R_1R_2 X^+$, where $Y^+$ comprises O, S or Se, $X^+$ comprises a halogen, such as I, and $R_1$, $R_2$ and $R_3$ comprise aliphatic or aromatic moieties that can be further substituted with common substituents, e.g., substituents comprised of atoms with a high EUV photoabsorption cross-section (in the sense as described herein), such as I, Se, F, O (examples for $R_1R_2R_3X^+$ and $R_1R_2Y^+$ are described herein) and $A^-$ comprises the anion of a strong acid, comprising atoms with low EUV photoabsorption cross-sections (definition of "low" as described herein) such as C, H, N, S, B and selected from the group of peracceptor-substituted aromatic anions or carboranes (examples are pentacyanocyclopentadienide ($4.76 \times 10^5$ cm$^2$/mol, atom-avg.), camphorsulfonate ($3.20 \times 10^5$ cm$^2$/mol, atom-avg.), carborane $C_2B_{10}H_{12}^-$ ($1.09 \times 10^5$ cm$^2$/mol, atom-avg.)). Meagley, United States Patent Appl. 2005/0221220, describes carboranes.

The base quencher is selected from a group of compounds, comprising amines, t-butoxycarbonyl-protected amines or quaternary ammonium salts (examples are described herein).

In another aspect, the present invention comprises a photoresist formulation comprising:

(a) a resist polymer that is originally insoluble in aqueous, alkaline developers, but becomes soluble in the developer upon reaction with acid, under conditions specific for the particular resist polymer;

(b) an ionic photoacid generator $P^+ A^-$, in which $A^-$ contains atoms with low EUV photoabsorption cross-sections ("low" as defined herein);

(c) a small amount of a base quencher (as defined herein).

In the invention; including the aspect of the invention described immediately above, the resist polymer comprises polymers as described herein. The photoacid generator has the general structure $P^+ A^-$, where $P^+$ comprises an organic cation of the general structure $R_1R_2R_3 Y^+$, or an organic halonium cation of the general structure $R_1R_2X^+$, where $Y^+$ comprises O, S or Se, $X^+$ comprises a halogen, such as I, and $R_1$, $R_2$ and $R_3$ comprise aliphatic or aromatic moieties that can be further substituted with common substituents; and $A^-$ comprise the anion of a strong acid having atoms with low EUV photoabsorption cross-sections (definition of "low" as described herein); such as C, H, N, S, B (examples described herein). The base quencher is selected from a group of compounds, comprising amines, t-butoxycarbonyl-protected amines or quaternary ammonium salts (examples as described herein).

Additional features, objectives, and advantages of the invention are set forth in, and will be apparent from this written description, or may be learned by practice of this invention and realized and obtained by the compounds, compositions and processes generally, and as pointed out not only in this written description, but also the claims that follow, the abstract of the disclosure and the drawings.

BRIEF DESCRIPTION OF THE DRAWINGS

The accompanying Figures where like reference numerals refer to identical or functionally similar elements throughout the separate views are incorporated into this specification, which together with the detailed description herein serve to further illustrate various embodiments and to explain various principles and advantages of the present invention.

In FIG. 3, MADMA-NORLAC stands for the copolymer poly([2-methyl-2-adamantyl methacrylate]-co-[5-methacryloyloxy-2,6-norbornane carbolactone]). In FIG. 4, ESCAP comprises poly(4-hydroxystyrene-co-tert-butyl acrylate) 65/35.

DETAILED DESCRIPTION OF THE INVENTION

Figure 1:
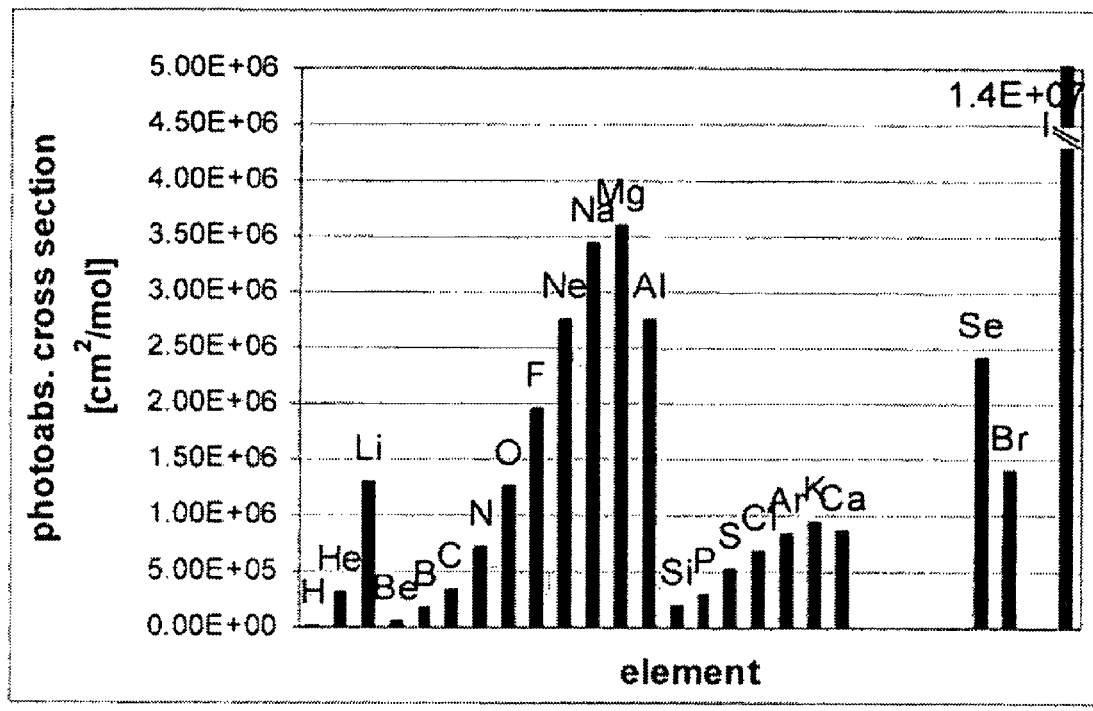
FIG. 1 shows photoabsorption cross-sections for EUV photons (13.5 nm; 92 eV), based on data from the calculator at http://henke.lbl.gov/optical_constants/pert_form.html.

To achieve these and other advantages, and in accordance with the purpose of this invention as embodied and broadly described herein, the following detailed embodiments as examples are disclosed that can be embodied in various forms. The specific compounds, compositions, processes and structural details set out herein comprise a basis for the claims and a basis for teaching one skilled in the art to employ the present invention in any novel and useful way. The terms, phrases and Figures are also set out herein to provide an understandable description of how to make and use this invention.

The preset invention comprises novel photoacid generators to be formulated into polymer compositions that are useful in lithographic processes, especially when EUV photons are used. In carrying out the present invention, conventional materials and processing techniques can be employed and, hence, such conventional aspects are not set forth herein in detail. For example, the selection of suitable resist polymers, bases and solvents is conducted in a conventional manner. One having ordinary skill in the art once aware of the present disclosure could employ suitable formulation, coating and exposure techniques without undue experimentation.

In another aspect, the invention comprises PAGs optimized for EUV photoabsorption. In the structures described in greater detail below, $P^+$ is significantly higher absorbing for EUV photons; or $A^-$ consists only of atoms with a low photoabsorption cross-section for EUV, while still being an anion of a very strong acid; or a combination of the two. The terms "high" and "low" photoabsorption cross-section for EUV, wherever mentioned in this section, refer to atom-averaged EUV absorption cross-section>$5\times10^5$ cm$^2$/mol and atom-averaged EUV absorption cross-section<$5\times10^5$ cm$^2$/mol, respectively, as calculated according to FIG. 1.

In the present invention, components of PAGs are strategically selected for absorption characteristics required for EUV photons. One set of components of such PAGs acts as an antenna for EUV photons and can comprise atoms with high EUV photoabsorption cross-sections. This component decomposes upon reaction with photons under formation of a proton, and this proton forms a strong acid by combination with another component of the PAGs. This other component of such PAGs which becomes part of the newly formed acid can comprise atoms with low EUV photoabsorption cross-sections; or, as a combination, the set of PAG components acting as antenna for EUV photons comprising atoms with high EUV photoabsorption cross-sections and the set of PAG components becoming part of the newly formed acid comprising atoms with low EUV photoabsorption cross-sections according to FIG. 1.

Formulation of such PAGs into photoresists leads to enhanced photospeed of the resists when irradiated with EUV photons, compared to photoresist formulations with conventional PAGs.

The PAG components acting as antennae for EUV photons comprises organic onium cations selected from organic chalconium cations of the general structure $R_1R_2R_3Y^+$, where $Y^+$ comprises oxygen (O), sulfur (S), selenium (Se), or tellurium (Te) and of organic halonium cations of the general structure $R_1R_2X^+$, where $X^+$ comprises a halogen, such as iodine (I). In the onium cations, $R_1$, $R_2$ and $R_3$ comprise aliphatic or aromatic moieties that can be further substituted with common substituents, such as halogens, such as fluorine (F) or iodine (I), alkyl, alkyloxy, aryl, aryloxy, nitro, cyano, halogen-substituted alkyl or halogen-substituted alkyloxy, and the like.

This invention encompasses such onium cations that comprise atoms $X^+$ or $Y^+$ and/or substituents $R_1$, $R_2$, $R_3$ characterized by a high EUV photoabsorption cross-section. The other PAG component of the invention is characterized as one that remains as a weakly coordinating and/or delocalized anion upon completion of the photochemical decomposition of the herein described PAGs. Examples of such anions are organic sulfonates $R_4$—$SO_3^-$ (in which $R_4$ comprises perfluoroalkyl or substituted or unsubstituted aryl or heteroaryl groups) and peracceptor-substituted anions 4, 5, 6 or 7:

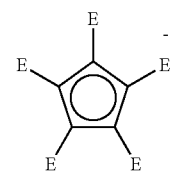

4

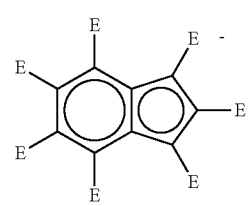

5

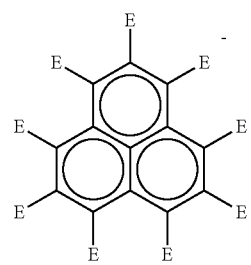

6

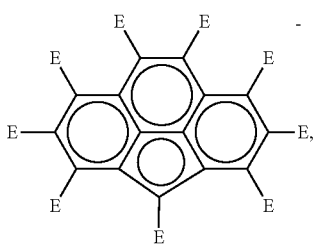

7 where E represents a strong electron-withdrawing substituent, particularly the cyano group CN. At least one substituent E can also be represented by another group, including but not limited to hydrogen, alkyl, alkyloxy, alkyloxycarbonyl, nitro or a halogen. One example of such peracceptor-substituted anions is compound 8, which corresponds to compound 4 with all E represented by cyano groups (CN):

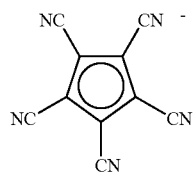

8

The synthesis and properties of this pentacyanocyclopentadienide anion (4) are described in the literature (O. Webster, *J. Am. Chem. Soc.* 1966, 88, 4055; O. Webster, U.S. Pat. No. 3,853,943; H. E. Simmons, et al., *J. Org. Chem.* 1980, 45, 5113; C. Richardson, C. Reed, *Chem. Common.* 2004, 706).

Such anions in conjunction with protons form very strong acids that comprise, e.g., sulfonic acid $R_4$—$SO_3H$ (in which $R_4$ comprises perfluoroalkyl or substituted or unsubstituted aryl or heteroaryl groups), carboranes and peracceptor-substituted cyclic organic compounds, such as 4a, 5a, 6a or 7a, which are characterized by the generation of aromaticity upon removal of the one remaining hydrogen atom:

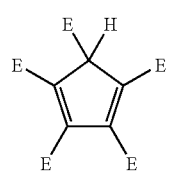

4a

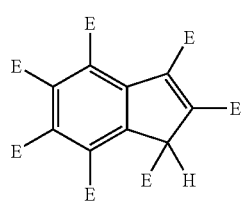

5a

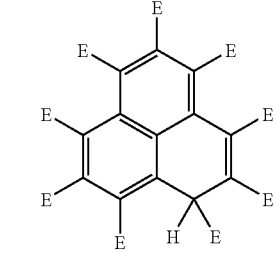

6a

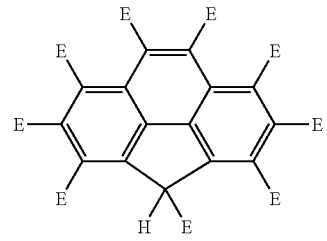

7a

Calculations of the acids 4a, 5a, 6a, and 7a with E=CN(R. Vianello, Z. Maksic, *Tetrahedron* 2005, 61, 9381) have shown that all of these are—in the gas phase—super acids (i.e., acids of greater acidity than 100% $H_2SO_4$) with pKa values ranging from −13 to −23. Therefore, anion 4 (and in some instances the anions of 6, 7 and 8 as well) is very well suited for the application as PAGS, particularly for EUV due to the comparably low photoabsorption of carbon and nitrogen, but has not yet been used as such.

An example of the cyclic, peracceptor-substituted organic anions to which this class is not limited, comprises the group of compounds 4, 5, 6, and 7, in which E comprises an electron-withdrawing group, such as the cyano group (CN). However, the electron-withdrawing, group is not limited to the cyano group (CN), but all E can be independent from each other, and at least one group E can also be represented by an alkyl, alkyloxy, hydrogen, nitro, alkoxycarbonyl, halogen, aryl, aryloxy or aryloxycarbonyl group.

In a further aspect, the invention comprises ionic PAGs of the general structure $P^+ A^-$, where:

I-$P^+$ comprises an organic sulfonium, selenium or halonium, comprising iodonium, cation of the general structure $R_1R_2R_3S^+$, $R_1R_2R_3Se^+$ or $R_1R_2X^+$, respectively, where $R_1R_2R_3$ comprise aliphatic or aromatic moieties that can be unsubstituted or substituted with common substituents, such as halogens, comprising fluorine, alkyl, alkoxy, aryl, aryloxy, nitro, alkyl or aryloxo, or alkyloxy- or aryloxy carbonyl groups, $X^+$ comprises halogen; or, $R^1$ and $R^2$ comprise collectively a $C_2$-$C_{30}$ linear or branched alkylene $(CH_2)_n$ chain and $R^3$ comprises at least one of Ar and Ar—CO—$CH_2$—, where Ar comprises an aryl group, optionally substituted with common substituents, such as OH, branched, linear or cyclic alkyl or branched, linear or cyclic alkyloxy; specifically in form of the S-aryl-tetrahydrothiophenium cation (9).

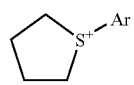

9 where Ar is an aromatic group, or a substituted aromatic group.

In one embodiment the substituents of the groups $R_1$, $R_2$, and $R_3$, comprise atoms with high photoabsorption cross-sections in EUV as shown in FIG. 1. However, such cation $P^+$ can also have low photoabsorption cross-section in EUV when used in conjunction with an anion $A^-$ with low photoabsorption cross-section in EUV.

Additionally, $A^-$ may comprise the anion of a very strong organic acid. Such acid in one embodiment comprises atoms with low photoabsorption cross-sections in EUV as shown in FIG. 1. Generally, such anions can comprise cyclic organic compounds, per-substituted with electron-withdrawing groups E, in which the ring-protonation destroys aromaticity. Examples of this class of anions, comprise compounds 4, 5, 6 and 7 as follows:

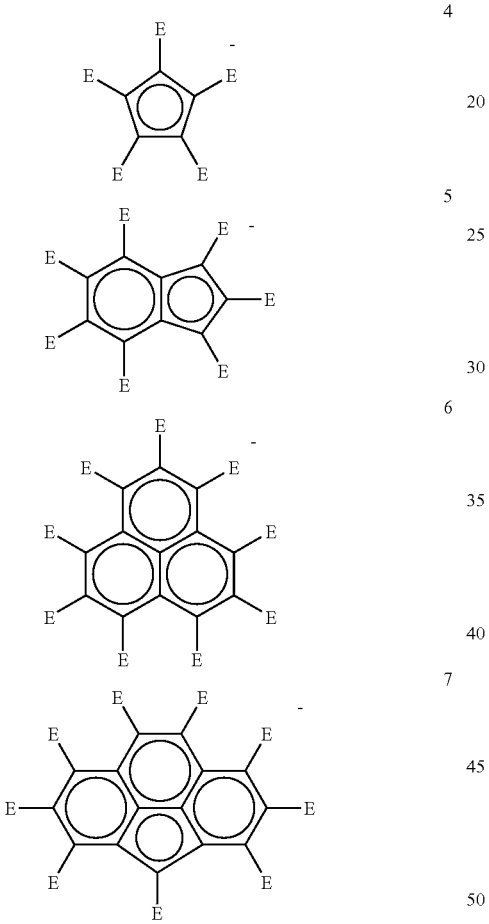

where E comprises a strong electron-withdrawing substituent, and in one embodiment this substituent comprises low photoabsorption cross-section in EUV, comprising the cyano group CN. However, the electron-withdrawing group is not limited to the cyano group (CN), but E can be the same or different. Other substituents, E, comprise an alkyl, alkyloxy, hydrogen, nitro, alkoxycarbonyl, halogen, aryl, aryloxy or aryloxycarbonyl group. These anions with low EUV absorption are not limited to the anions 4, 5, 6 and 7, but could be anions of carboranes and other art-known anions as well that also exhibit low EUV absorption. R. P. Meagley, United States Patent Appl. 2005/0221220 gives examples of such carboranes.

Disclosed anions $A^-$, however, can also comprise aliphatic sulfonates, comprising perfluoroaliphatic sulfonates, substituted or unsubstituted arylsulfonates, when used in conjunction with a cation $P^+$ that comprise atoms with high photoabsorption cross-section in EUV light.

PAGs $P^+ A^-$ of the invention comprise cations $P^+$, atoms with high photoabsorption cross-section in EUV, such as the above-mentioned sulfonium, selenium or iodonium cations comprising fluorine as substituents of the groups $R_1$, $R_2$, and/or $R_3$, and of anions $A^-$ comprising atoms with low photoabsorption cross-section in EUV, comprise, e.g., such above-mentioned cyclic organic anions that are substituted with strong electron withdrawing groups, comprising e.g. CN.

II. Specifically, and in one embodiment, PAGs $P^+ A^-$, comprise:

1. $P^+$ comprising;
   a) a sulfonium cation, comprising,

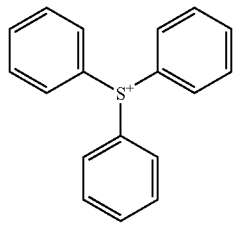

b) a selenium cation, comprising;

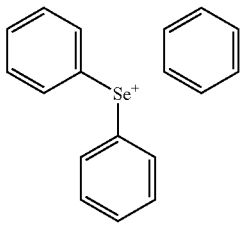

c) an iodonium cation, comprising,

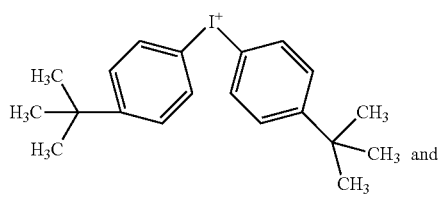

and d)

2. $A^-$ comprises the anion of a very strong acid, comprising:

a)
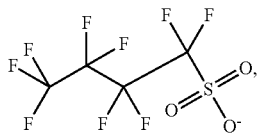

b)
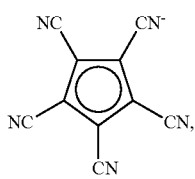

The compound

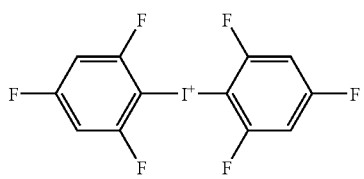

not only functions in PAGs used in lithographic methods that employ EUV radiation as the exposure radiation, but also is effective in optical lithography such as lithography using 248 nm exposure radiation, and 193 nm exposure radiation as well.

For the PAGs in the combinations $P^+ A^-$ with $P^+$=1a or 1c and $A^-$=2b, $P^+$ comprises cations used in commercially available PAGs, and $A^-$ comprises an anion of a superacid that has very low EUV absorbance.

For the PAGs in the combinations $P^+ A^-$ with $P^+$=1b or 1d and $A^-$=2a, $P^+$ comprises cations of higher (1b) or extremely high (1d) photon absorption in EUV, and $A^-$ comprises an anion used in commercially available PAGs.

For the PAGs in the combinations $P^+ A^-$ with $P^+$=1b or 1d and $A^-$=2b, $P^+$ comprises cations of higher (1b) or extremely high (1d) photon absorption in EUV, and $A^-$ comprises an anion of a superacid that has very low EUV absorbance. It is intended that the foregoing description does not include art known PAG compounds or their use in EUV photolithography.

The above mentioned PAGs in II, have been synthesized, characterized and formulated into polymeric photoresists. Acid generation has been demonstrated through titration experiments and dose-to-clear experiments of both optical (248 nm, 193 nm) and EUV lithography.

In summary, this invention encompasses acid-forming PAG components comprising atoms or substituents $R_4$ or E that are characterized by a low EUV photoabsorption cross-section.

EXAMPLES

The following examples illustrate embodiments of the invention.

Example 1

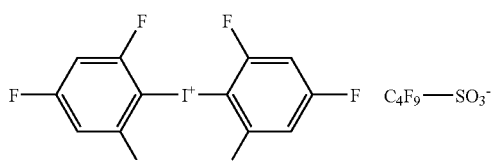

Materials synthesis (Bis(2,4,6-trifluorophenyl)iodonium perfluorobutanesulfonate, 10 [DTFPIO PFBuS]): According to the method by Beringer et al. (J. Am. Chem. Soc. 81, 342 (1959)), 2 mmol (0.51 g) iodine and 6 mmol (1.3 g) KIO$_3$ were mixed in a 50 ml round-bottom flask and stirred with 10 ml conc. H$_2$SO$_4$. The reaction was continued at room temperature, until the dark brownish color of iodine had completely disappeared and a yellowish solid of (IO)$_2$SO$_4$ formed. Subsequently, 10 mmol (1.3 g) of 1,3,5-trifluorobenzene was added to the (IO)$_2$SO$_4$ suspension in H$_2$SO$_4$ and the mixture was stirred at 55° C. for 20 h. The solution was then added drop-wise to 100 ml H$_2$O and the precipitate filtered off. The obtained aqueous solution of bis(2,4,6-trifluorophenyl)iodonium hydrogensulfate was further extracted with ether (1×) and benzene (1×). Subsequent addition of aqueous solution of potassium perfluorobutanesulfonate to the aqueous reaction mixture gave a white, crystalline precipitate that was thoroughly washed with water and dried in an oil pump vacuum for 16 h.

Example 2

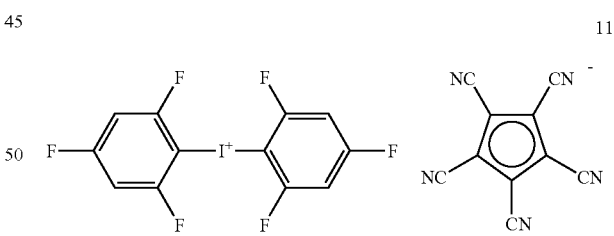

Material synthesis (Bis(2,4,6-trifluorophenyl)iodonium pentacyanocyclopentadienide, 11 [DTFPIO CN5]): To 0.45 g NaH (60% in min. oil) in 35 ml dimethoxyethane was added 0.91 g methyl cyanoacetate under N$_2$. Once hydrogen evolution had ceased, 2.83 g of 2,3,5,6-tetracyano-1,4-dithiin, prepared according to the literature (C. Richardson, C. Reed, Chem. Commun. 706 (2004); H. E. Simmons, et al., J. Org. Chem. 45, 5113 (1980)), was added. The mixture was stirred at 110° C. for 30 min, then heated up to 160° C. until the solvent was evaporated. Remaining traces of solvents were removed in oil pump vacuum, until a dark brown, dry solid was formed. This solid was dissolved in 100 mL of water, followed by addition of 5 mL conc. $H_2SO_4$. Filtration from the dark brown solids yielded a reddish solution that was discolored by addition of 2 mL of 30% $H_2O_2$ and heating to 80° C. for 60 min. The obtained solution of sodium pentacyanocyclopentadienide was then cooled to room temperature and filtered; excessive $H_2O_2$ was destroyed with $Na_2SO_3$, while a strong acidic pH was maintained. Addition of an aqueous solution of bis(2,4,6-trifluorophenyl)iodonium hydrogensulfate, prepared as in Example 1, gave a yellowish precipitate that was filtered, dried and recrystallized from acetone/ether.

Example 3

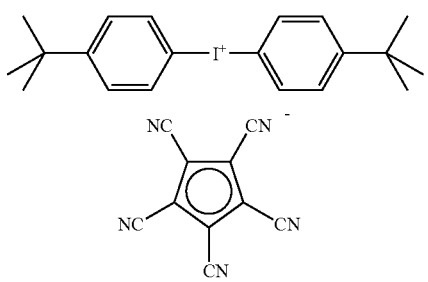

12

Material synthesis (Bis(4-tert-butylphenyl)iodonium pentacyanocyclopentadienide, 12 [DTBPIO CN5]): To an aqueous solution of sodium pentacyanocyclopentadienide, prepared as described in Example 2, was added an aqueous solution of bis(4-tert-butylphenyl)iodonium acetate. The obtained yellow is precipitate was filtered, dried and recrystallized from acetone/ether.

Example 4

Formulation and film formation: A propyleneglycolmonomethylether acetate (PGMEA) solution of 10 wt % poly(4-hydroxystyrene-co-tertbutyl acrylate) (65/35; ESCAP), bis(2,4,6-trifluorophenyl)iodonium perfluorobutanesulfonate (DTFPIO PFBuS), 10, in an amount equimolar to 0.4 wt % TPS PFBuS and tetrabutylammonium hydroxide (TBAH) (base quencher; used in very small quantities to quench acid that migrates into unexposed regions, thereby improving image quality) was prepared. TBAH was used in a PAG:TBAH=1.0.05 molar ratio. A silicon wafer (5") was coated with 0.8 nm AR3-600 (3000 rpm, then baking at 220° C. for 1 min.), followed by coating with the resist solution (1400 rpm, then baking at 130° C. for 1 min). The obtained film thickness was 220 nm.

Example 5

Dose-to-Clear Experiment: EUV exposures were performed on an EQ-10M EUV light source (Energetiq Technology Inc.), using Xe gas discharge-produced plasma that provides 10 W into 2 pi in-band EUV irradiation (within 2% bandwidth). Long wavelength out-of-band radiation was blocked by a Zr filter (thickness: 200 nm). A sample, consisting of 5×¾ inch piece of a wafer, coated with a photoresist film prepared as described in Example 4 was mounted at a 90° angle with respect to the beam and was irradiated with an in-band EUV intensity of 2 $mW/cm^2$. After incremental steps of EUV exposure, the sample was baked at 120° C. for 1 min, developed with 0.26 M tetramethylammonium hydroxide (TMAH) for 45 s and finally rinsed with de-ionized water. Function of the base used in such developer solutions is to dissolve reacted, soluble resist polymer. The film thickness of the unexposed and exposes areas was measured on a Nano-Spec (Model 4000; Nanometrics, Inc.). Dose to clear was 1.2 $mJ/cm^2$.

Example 6

Figure 2:
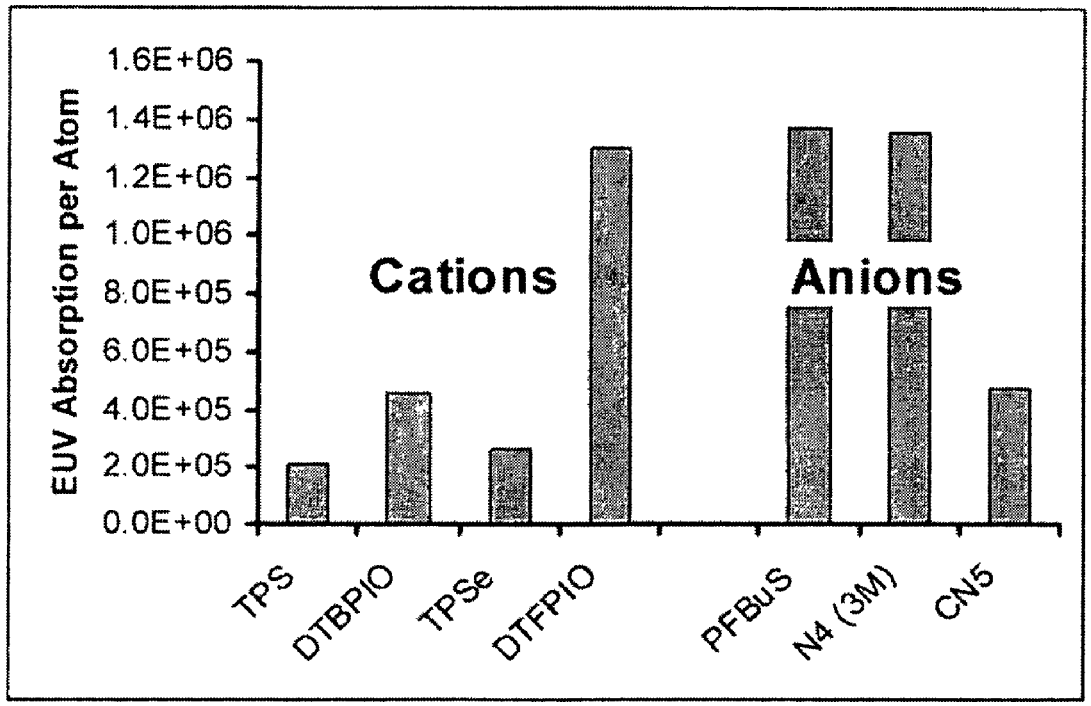
FIG. 2 shows EUV photoabsorption cross-sections for selected PAG components, averaged per atom of the corresponding component. Examples of $P^+$ cations shown in FIG. 2 are triphenylsulfonium (TPS), bis(4-tert.-butylphenyl)iodonium (DTBPIO), triphenylselenium (TPSe) and bis(2,4,6-trifluorophenyl)iodonium (DTFPIO). Examples of $A^-$ anions shown in FIG. 2 are perfluorobutanesulfonate (PFBuS), bis(perfluorobutanesulfone)imidate (N4(3M)) and pentacyanocyclopentadienide (CN5).
Figure 3:
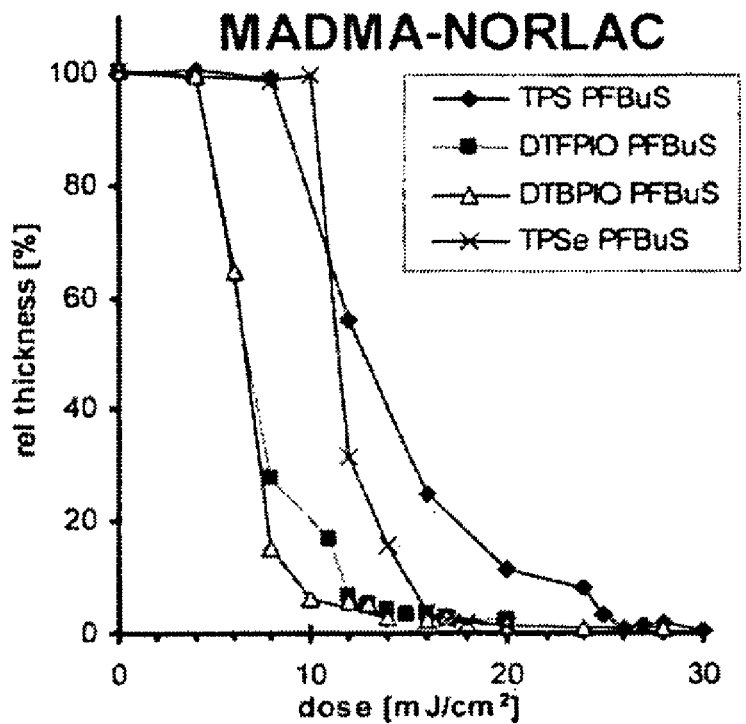
FIG. 3 and FIG. 4 show EUV dose to clear measurements of commercially available PAGs compared to the novel PAGs of this invention.
Figure 4:
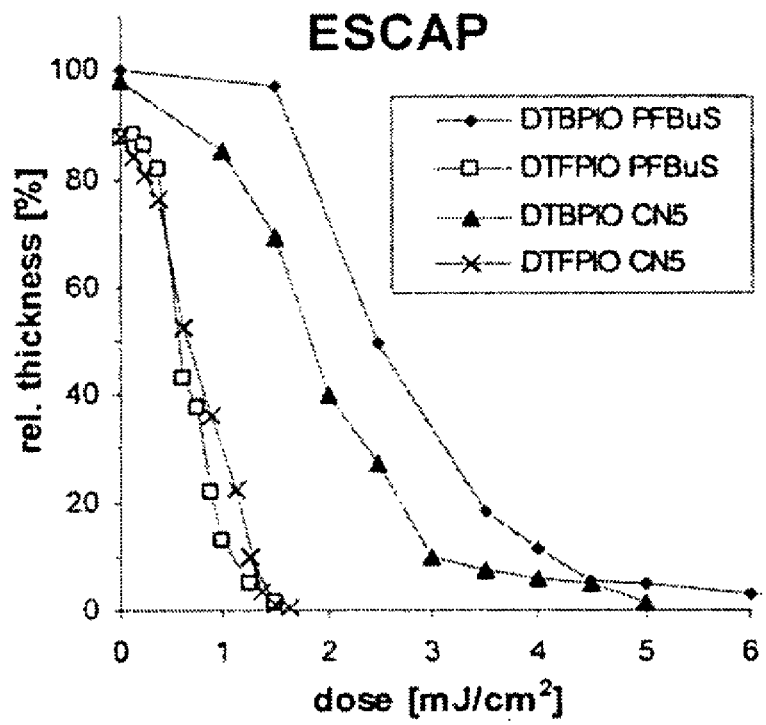
Figure 5:
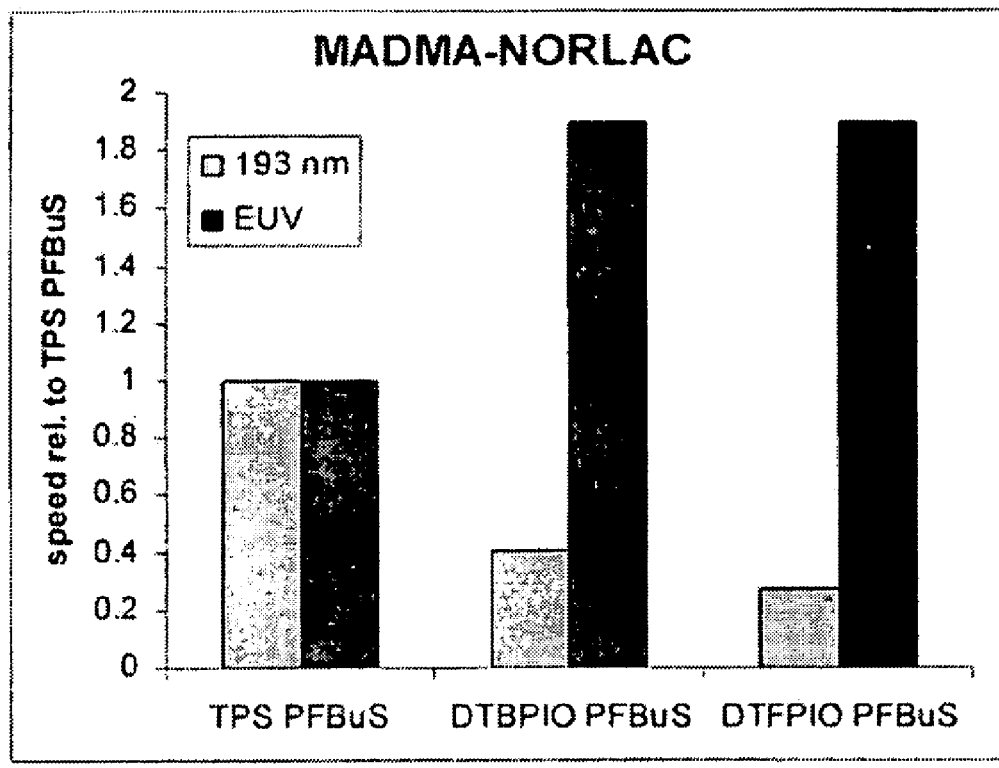
FIGS. 5 and 6 show $E_{1/2}$ data relative to commercial PAGs (=1) and (a) photospeed in EUV is not related to speed at 248 nm or 193 nm, (b) support the concept that EUV specific PAGs have to be designed.
Figure 6:
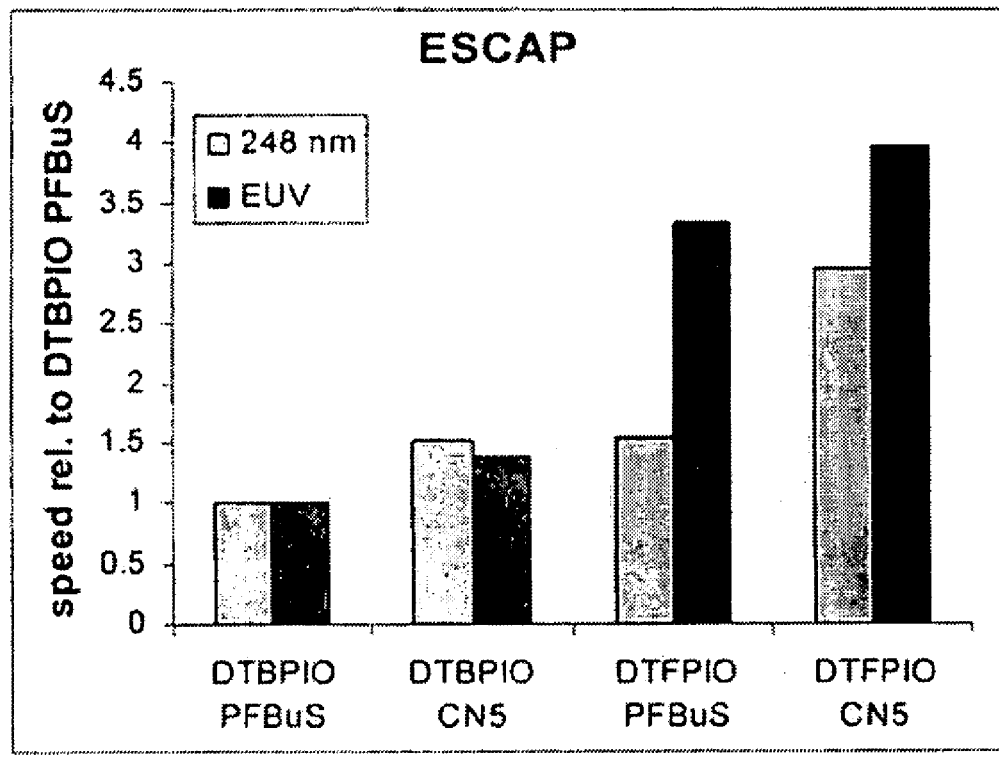
Figure 7:
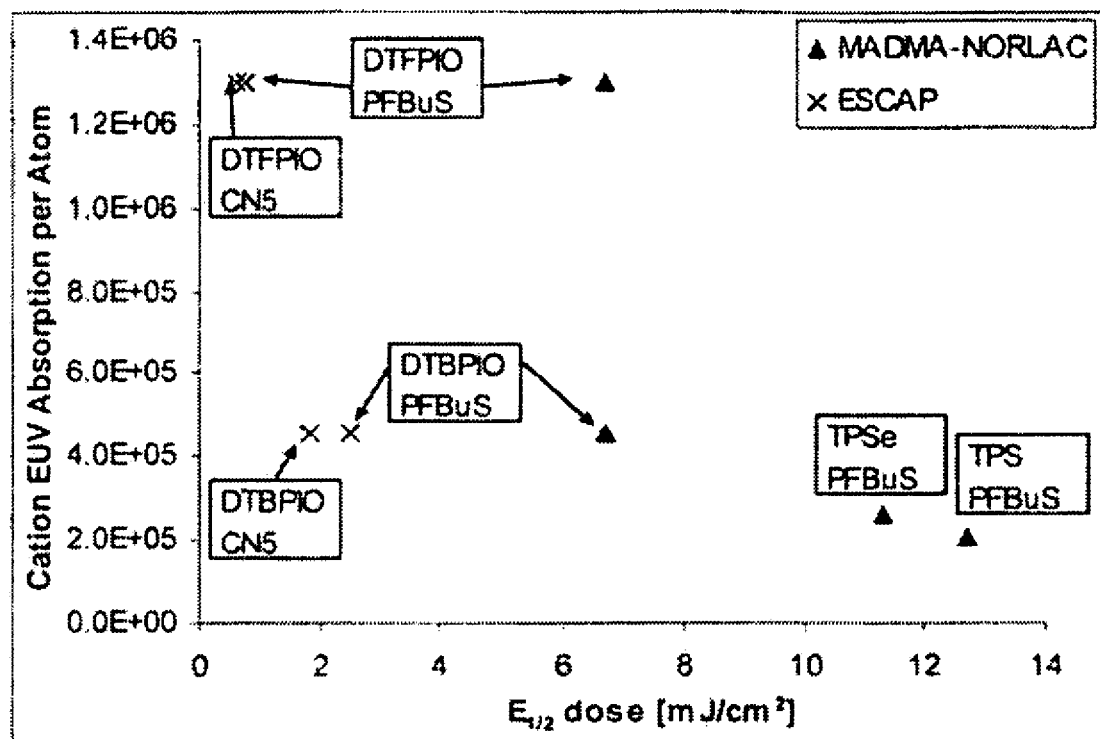
FIG. 7 shows EUV photospeed correlated with EUV absorption by the PAG cation, and further EUV photospeed increases when EUV absorption by the PAG cation increases.

Dose-to-Clear Experiment with Commercial PAG: A sample prepared as described in Example 4 and exposed in the same fashion as described in Example 5 but containing commercially available bis(4-tert-butylphenyl)iodonium perfluorobutanesulfonate (DTBPIO PFBuS) cleared at 4.5 $mJ/cm^2$. Atom-averaged EUV photoabsorption cross-sections for the DTFPIO and DTBPIO cations are shown in FIG. 2.

Example 7

Dose-to-Clear Experiment: A sample is prepared and exposed in the same fashion as described in examples 4 and 5 but containing bis(2,4,6-trifluorophenyl)iodonium pentacyanocyclo-pentadienide (DTFPIO CN5), 11, cleared at 1.2 $mJ/cm^2$. Atom-averaged EUV photoabsorption cross-sections for the CN5 and PFBuS anions are shown in FIG. 2.

Example 8

Dose-to-Clear Experiment: A sample is prepared and exposed in the same fashion as described in examples 4 and 5 but containing bis(4-tert-butylphenyl)iodonium pentacyanocyclo-pentadienide (DTBPIO CN5), 12, cleared at 1.2 $mJ/cm^2$.

Example 9

Dose-to-Clear Experiment: A sample is prepared and exposed in the same fashion as described in Examples 4 and 5 but containing poly([2-methyl-2-adamantyl methacrylate]-co-[5-methacryloyloxy-2,6-norbornane carbolactone] and bis(2,4,6-trifluorophenyl)iodonium perfluorobutanesulfonate, 10, cleared at 10.0 $mJ/cm^2$.

Example 10

Dose-to-Clear Experiment with Commercial PAG: A sample prepared and exposed in the same fashion as described in Examples 9 but containing commercially available triphenylsulfonium perfluorobutanesulfonate cleared at 20.0 $mJ/cm^2$.

Examples 9 and 10 describe experiments with a formulation comprising a polymer with higher protection ratio, which explains why both dose-to-clear values are higher than in the other examples.

As noted before, the invention generally and specifically defines high EUV photoabsorption and low EUV photoabsorption, and when used in this written description, high EUV photoabsorption and low EUV photoabsorption refer to all definitions, and the general definitions are included in addition to those instances where specific definitions of high EUV photoabsorption and low EUV photoabsorption are given. The compounds of the invention also include various organic and other moieties per se, but are also intended to include organic or other moieties that can be further substituted with substituents; where these organic and other moieties, and/or substituents comprise inter alia, aryl groups, alkyl groups; halogens, such as fluorine (F) or iodine (I), as well as bromine (Br), or chlorine (Cl), alkyloxy, alkyloxo, aryloxy, arylcarbonyloxy, carboaryloxy, alkylcarbonyloxy, carbalkyloxy, aryloxy, nitro, cyano, halogen-substituted alkyl or halogen-substituted alkyloxy, substituted alkyl, alkylene, alicyclic, hydrocarbyl, cyclic alkyl (cycloaliphatic), hetero cycloaliphatic, aralkyl or alkaryl, alkoxy, acyl, acyloxy, alkylenoxy, such as defined inter alia by Allen et al., U.S. Pat. No. 7,193,023, col. 3, line 51 to col. 6, line 24, and Mizutani et al. U.S. Pat. No. 7,232,640, col. 8, line 54 to col. 12, line 14, and all other moieties and substituents defined by Allen et al., and/or Mizutani et al. For the purpose of this invention, these moieties and/or substituents also include combinations of moieties and/or substituents, such as two or more of the moieties and/or substituents. These references give ranges of carbon atoms that apply to the various substituents and/or moieties of this invention and the following discussion applies to these ranges as well as the combinations of moieties and/or substituents.

The invention also encompasses processes for using the compounds and compositions of the invention to form patterned material features on a substrate comprising a material surface which may comprise a metal conductor layer, a ceramic insulator layer, a semiconductor layer or other material depending on the stage of the manufacture process and the desired material set for the end product. The compounds and compositions of the invention are especially useful for lithographic processes used in the manufacture of integrated circuits on semiconductor substrates. The compounds and compositions of the invention used in lithographic processes create patterned material layer structures such as metal wiring lines, holes for contacts or vias, insulation sections (e.g., damascene trenches or shallow trench isolation), trenches for capacitor structures, ion implanted semiconductor structures for transistors, and the like as might be used in integrated circuit devices.

After exposure, the photoresist structure with the desired pattern is obtained (developed) by contacting the photoresist layer with an aqueous alkaline solution which selectively dissolves the areas of the photoresist which were exposed to radiation in the case of a positive photoresist (or the unexposed areas in the case of a negative photoresist). Some aqueous alkaline solutions (developers) comprise aqueous solutions of tetramethyl ammonium hydroxide. The resulting lithographic structure on the substrate is then typically dried to remove any remaining developer. If a top coat has been used, it can be dissolved by the developer in this step.

The pattern from the photoresist structure may then be transferred to the exposed portions of underlying material of the substrate by etching with a suitable etchant using techniques known in the art. In one embodiment the transfer is done by reactive ion etching or by wet etching. Once the desired pattern transfer has taken place, any remaining photoresist may be removed using conventional stripping techniques. Alternatively, the pattern may be transferred by ion implantation to form a pattern of ion implanted material.

Examples of general lithographic processes where the compound or composition of the invention may be useful are disclosed in U.S. Pat. Nos. 4,855,017; 5,362,663; 5,429,710; 5,562,801; 5,618,751; 5,744,376; 5,801,094; 5,821,469 and 5,948,570. Other examples of pattern transfer processes are described in Chapters 12 and 13 of "Semiconductor Lithography, Principles, Practices, and Materials" by Wayne Moreau, Plenum Press, (1988). It should be understood that the invention is not limited to any specific lithography technique or device structure.

Glodde et al., U.S. patent application Ser. No. 11/970,073 filed Jan. 8, 2008, describes other art-known photolithographic processes, polymers, solvents additives and the like useful in the process and formulations of the present invention.

Throughout this specification, abstract of the disclosure, and in the drawings the inventor has set out equivalents, including without limitation, equivalent elements, materials, compounds, moieties, substituents, compositions, conditions, processes, structures and the like, and even though set out individually, also include combinations of these equivalents such as the two component, three component, or four component combinations, or more as well as combinations of such equivalent elements, materials, compounds, moieties, substituents, compositions conditions, processes, structures and the like in any ratios or in any manner.

Additionally, the various numerical ranges describing the invention as set forth throughout the specification also includes any combination of the lower ends of the ranges with the higher ends of the ranges, and any single numerical value, or any single numerical value that will reduce the scope of the lower limits of the range or the scope of the higher limits of the range, and also includes ranges falling within any of these ranges.

The term "about," "substantial," or "substantially" as applied to any claim or any parameters herein, such as a numerical value, including values used to describe numerical ranges, means slight variations in the parameter. In another embodiment, the terms "about," "substantial," or "substantially," when employed to define numerical parameter include, e.g., a variation up to five per-cent, ten per-cent, or 15 per-cent, or somewhat higher or lower than the upper limit of five per-cent, ten per-cent, or 15 per-cent. The term "up to" that defines numerical parameters means a lower limit comprising zero or a miniscule number, e.g., 0.001. The terms "about," "substantial" and "substantially" also mean that which is largely or for the most part or entirely specified. The inventor also employs the terms "substantial," "substantially," and "about" in the same way as a person with ordinary skill in the art would understand them or employ them. The phrase "at least" means one or a combination of the elements, materials, compounds, or conditions, and the like specified herein, where "combination" is defined above The terms "written description," "specification," "claims," "drawings," and "abstract" as used herein refer to the written description, specification, claims, drawings, and abstract of the disclosure as originally filed, and if not specifically stated herein, the written description, specification, claims, drawings, and abstract of the disclosure as subsequently amended.

All scientific journal articles and other articles, including internet sites, as well as issued and pending patents that this written description mentions including the references cited in such scientific journal articles and other articles, and such patents, are incorporated herein by reference in their entirety and for the purpose cited in this written description, and for all other disclosures contained in such scientific journal articles and other articles as well as patents and the aforesaid references cited therein, as all or any one may bear on or apply in whole or in part, not only to this written description, but also the abstract, claims, and appended drawings of this application.

Although the inventor has described his invention by reference to some embodiments, other embodiments defined by the doctrine of equivalents are intended to be included as failing within the broad scope and spirit of the foregoing written description and the following claims, abstract of the disclosure, and drawings.

I claim:

1. A photoacid generator compound $P^+ A^-$, comprising:
   an antenna group $P^+$ comprising a cation with atom-averaged EUV photoabsorption cross-sections, and $A^-$ comprising an anion with atom-averaged EUV photoabsorption cross-sections; wherein said atom-averaged EUV photoabsorption cross-sections of said antenna group $P^+$ are greater than or substantially the same as said atom-averaged $A^-$ EUV photoabsorption cross-sections.

2. The photoacid generator of claim 1 wherein $A^-$ comprises $R-S0_3H$, wherein R comprises perfluoroalkyl or substituted or unsubstituted aryl or heteroaryl groups.

3. The photoacid generator of claim 1, wherein $P^+$ comprises an organic chalconium cation of the general structure $R_1, R_2, R_3 Y^+$, wherein $R_1, R_{2i}$, and $R_3$ comprise aliphatic or aromatic moieties optionally containing a substituent, and $Y^+$ comprises O, S or Se.

4. The photoacid generator of claim 3, wherein $Y^+$ has a high EUV photoabsorption cross-section.

5. The photoacid generator of claim 3, wherein $R_1$, $R_2$ and $R_3$ comprise aliphatic or aromatic moieties optionally comprising at least one substituent selected from halogen, alkyl, alkyloxy, aryl, aryloxy, nitro, cyano, halogen-substituted alkyl or halogen-substituted alkyloxy.

6. The photoacid generator of claim 5, wherein the substituents $R_1$ $R_2$ or $R_3$ are substituted with high EUV photoabsorption cross-section atoms selected from fluorine or iodine.

7. The photoacid generator of claim 1, wherein $P^+$ comprises an organic halonium cation of the general structure $R-IR_2X^+$, wherein $R_1$ and $R_2$ comprise aliphatic or aromatic moieties, and $X^+$ comprises a halogen.

8. The photoacid generator of claim 7, wherein $X^+$ has a high EUV photoabsorption cross-section.

9. The photoacid generator of claim 7, wherein $R_1$ and $R_2$ comprises aliphatic or aromatic moieties optionally including at least one substituent comprising halogen, alkyl, alkyloxy, aryl, aryloxy, nitro, cyano, halogen-substituted alkyl or halogen-substituted alkyloxy.

10. The photoacid generator of claim 9, wherein the substituents $R_1$ and $R_2$ are substituted with atoms having a high EUV photoabsorption cross-section and are selected from atoms comprising fluorine or iodine.

11. A photoacid generator compound $P^+ A^-$ of claim 1 comprising:
   a) an antenna group $P^+$ and
   b) $A^-$ comprises an acid-forming group comprising atoms with low EUV photoabsorption cross-sections according to FIG. 1.

12. The photoacid generator compound of claim 11, wherein $P^+$ comprises an organic chalconium cation of the general structure $R_1, R_2, R_3 Y^+$, wherein $Y^+$ comprises at least one substituent selected from O, S or Se and $R_1, R_2$, and $R_3$ comprise at least one substituent selected from aliphatic or aromatic moieties optionally comprising at least one substituent selected from halogen, alkyl, alkyloxy, alkoxy, aryl, aryloxy, nitro, alkyloxy, aryloxy, alkoxy carbonyl, cyano, halogen-substituted alkyl or halogen-substituted alkyloxy.

13. The photoacid generator compound of claim 11, wherein $R^1$ and $R^2$ comprise collectively a $C_2$-$C_{30}$ linear or branched alkylene $(CH_2)_n$ chain. $R^3$ comprises at least one of Ar and Ar—CO—$CH_2$—, where Ar comprises at least one substituent selected from an aryl group, optionally comprising substituents, selected from at least one of OH, branched, linear or cyclic alkyl or branched, linear or cyclic alkyloxy, or:

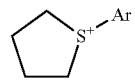

wherein Ar comprising an optionally substituted aromatic group.

14. The photoacid generator of claim 11, wherein $P^+$ comprises an organic halonium cation of the general structure $RTR_2X^+$ wherein $X^+$ comprises a halogen and wherein R1 and $R_2$ comprise aliphatic or aromatic moieties optionally comprising at least one substituent selected from halogen, alkyl, alkyloxy, aryl, aryloxy, nitro, cyano, halogen-substituted alkyl or halogen-substituted alkyloxy.

15. The photoacid generator of claim 11, wherein $A^-$ comprises the anion of a carborane or peracceptor-substituted organic anions, selected from at least one compound comprising 4, 5, 6 or 7:

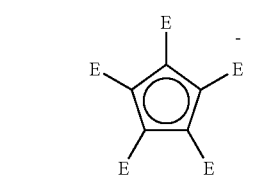

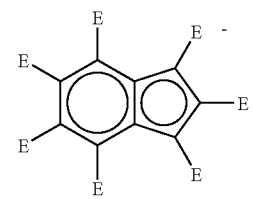

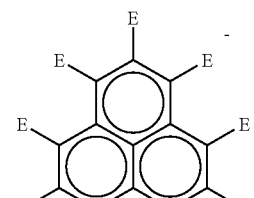

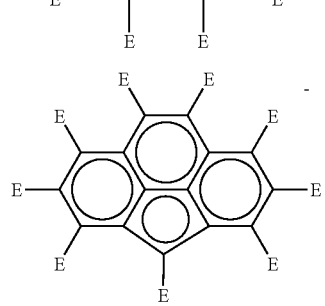

wherein E comprises an electron-withdrawing group and the ring-protonation eliminates aromaticity.

16. The photoacid generator of claim 15, wherein E comprises at least one of cyano (CN), alkyl, alkyloxy, hydrogen, nitro, alkoxycarbonyl, halogen, aryl, aryloxy or aryloxycarbonyl group, or atoms with low EUV photoabsorption cross-sections according to FIG. 1.

17. A photoacid generator compound P⁺ A' of claim 1 comprising:
   a) an antenna group P⁺ comprising atoms with high EUV photoabsorption cross-sections according to FIG. 1 comprising an organic chalconium cation of the general structure $R_1, R_2, R_3 Y^+$, wherein $R_1, R_{2i}$, and $R_3$ comprise aliphatic or aromatic moieties, optionally comprising at least one substituent selected from halogen, alkyl, alkyloxy, aryl, aryloxy, nitro, cyano, halogen-substituted alkyl halogen-substituted alkyloxy, fluorine, iodine, and $Y^+$ comprises O, S or Se, or
   b) an antenna group P⁺ comprising an organic halonium cation of the general structure $RiR_2X^+$, wherein F^ and $R_2$ comprise aliphatic or aromatic moieties optionally comprising at least one substituent selected from halogen, alkyl, alkyloxy, aryl, aryloxy, nitro, cyano, halogen-substituted alkyl or halogen-substituted alkyloxy, and $X^+$ comprises a halogen;
   c) an acid-forming group $A^{31}$ comprising atoms with low EUV photoabsorption cross-sections, comprised of, e.g., a carborane or a peracceptor-substituted aromatic anion, comprising at least one compound selected from 4, 5, 6 or 7:

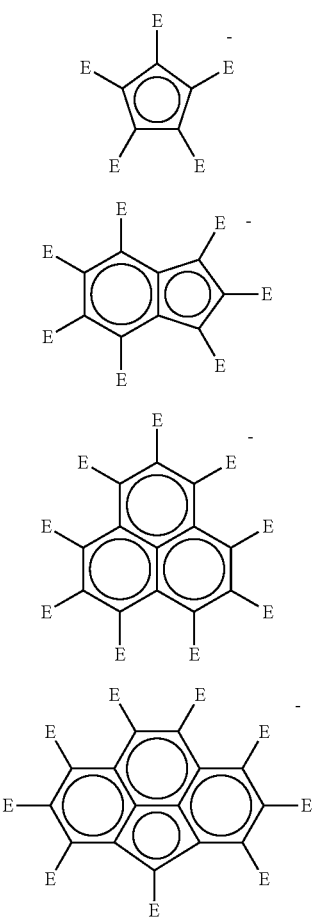

wherein E comprises at least one of cyano (CN), alkyl, alkyloxy, hydrogen, nitro, alkoxycarbonyl, halogen, aryl, aryloxy or aryloxycarbonyl, alkylcarbonyloxy, arylcarbonyloxy or atoms with low EUV photoabsorption cross-section according to FIG. 1.

18. A photoresist formulation, comprising:
   a) an acid-sensitive imaging polymer that is originally insoluble in aqueous, alkaline developers, but becomes soluble upon reaction with protons, with or without the aid of heating;
   b) a photoacid generator compound of claim 1;
   c) a small amount of a base quencher.

19. A photoacid generator compound P⁺ A⁻, of claim 11 wherein P⁺ is selected from;
   a) a sulfonium cation comprising,

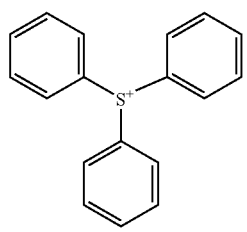

b) and A⁻ comprises an anion having low photoabsorption cross-sections in EUV.

20. A photoacid generator compound of claim 1 wherein P⁺ comprises a cation having high photoabsorption cross-sections in EUV and is selected from;
   a) a selenium cation comprising,

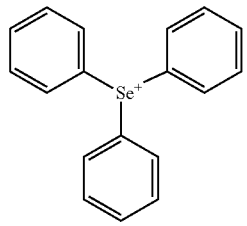

b) an iodonium cation comprising,

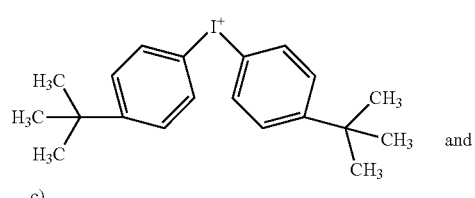 and c)

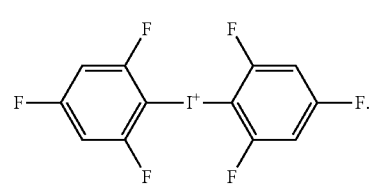.

21. The photoacid generator compound of claim 1 wherein the anion A⁻, comprises:

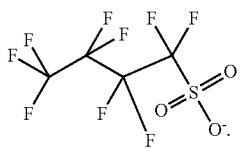

22. The photoacid generator compound of claim 11, wherein A⁻ comprises:

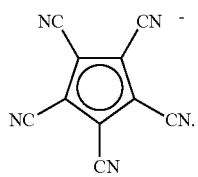

23. A photoacid generator compound P⁺ A⁻ comprising DTFPIO PFBuS said compound P⁺ A⁻, comprising: an antenna group P⁺ comprising a cation with atom-averaged EUV photoabsorption cross-sections, and A⁻ comprising an anion with atom-averaged EUV photoabsorption cross-sections; wherein said atom-averaged EUV photoabsorption cross-sections of said antenna group P⁺ are greater than or substantially the same as said A⁻ EUV photoabsorption cross-sections.

24. The photoacid generator compound of claim 1 comprising DTFPIO CN5.

25. The photoacid generator compound of claim 1 comprising DTBPIO CN5.

26. The photoresist formulation of claim 18 wherein said resist polymer comprises at least one of MADMA-NORLAC, ESCAP or poly ([N-(trifluoromethysulfonyl) methacrylamide]-co-[2-methyl- 2-adamantyl methacrylate]-co-[5-methacryloyloxy-2, 6-norbornane carbolactone]) (S1).

27. A method to improve the photospeed of lithographic imaging with EUV, comprising combining the photoacid generator of claim 1 with a photolithographic composition to obtain a formulation, applying said formulation to a substrate to obtain a treated substrate and exposing said treated substrate to EUV.

28. The method of claim 27 wherein the photoacid generator comprises said anion A⁻:

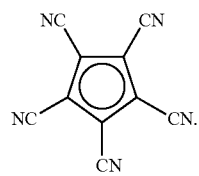

29. The method of claim 27 to improve the photospeed of lithographic imaging, comprising combining said photoacid generator with a photolithographic composition to obtain a formulation, applying said formulation to a substrate to obtain a treated substrate, and exposing said treated substrate to optical lithography radiation wherein said photoacid generator comprises one of:

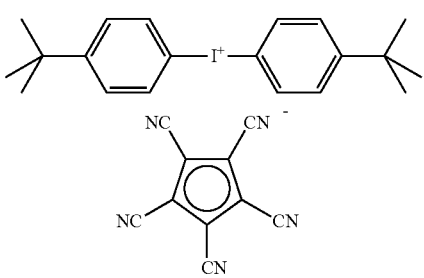

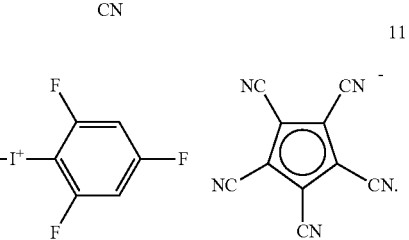

30. A photoacid generator compound P⁺ A⁻ of claim 1 comprising an antenna group P⁺ with atom-averaged EUV absorption cross-sections greater than about $5 \times 10^5$ cm²/mol.

* * * * *